(12) United States Patent
Yamada et al.

(10) Patent No.: US 7,867,198 B2
(45) Date of Patent: Jan. 11, 2011

(54) MEDICAL LIQUID INFUSION APPARATUS

(75) Inventors: Keiichi Yamada, Izumi (JP); Takeharu Kobayashi, Izumi (JP); Makoto Yoshida, Izumi (JP); Hiroshi Ihara, Izumi (JP)

(73) Assignee: Daiken Iki Kabushiki Kaisha (JP)

( * ) Notice: Subject to any disclaimer, the term of this patent is extended or adjusted under 35 U.S.C. 154(b) by 1001 days.

(21) Appl. No.: 11/660,257

(22) PCT Filed: Aug. 5, 2005

(86) PCT No.: PCT/JP2005/014381

§ 371 (c)(1),
(2), (4) Date: Feb. 15, 2007

(87) PCT Pub. No.: WO2006/018988

PCT Pub. Date: Feb. 23, 2006

(65) Prior Publication Data

US 2009/0137955 A1 May 28, 2009

(30) Foreign Application Priority Data

Aug. 16, 2004 (JP) .............................. 2004-236685

(51) Int. Cl.
*A61M 37/00* (2006.01)
(52) U.S. Cl. ...................................... 604/141
(58) Field of Classification Search ......... 604/140–144, 604/146–147, 70, 890.1, 891.1, 65–68
See application file for complete search history.

(56) References Cited

U.S. PATENT DOCUMENTS

| 5,064,413 | A | * | 11/1991 | McKinnon et al. ............ 604/70 |
| 6,458,102 | B1 | | 10/2002 | Mann et al. |
| 7,008,403 | B1 | | 3/2006 | Mallett |
| 2005/0209562 | A1 | * | 9/2005 | Kim ........................... 604/141 |

FOREIGN PATENT DOCUMENTS

| CN | 1266717 | 9/2000 |
| JP | H07-37194 | 7/1995 |
| JP | H09-262288 | 10/1997 |
| JP | 2004-008741 | 1/2004 |

* cited by examiner

*Primary Examiner*—Christopher D Koharski
(74) *Attorney, Agent, or Firm*—Gerald E. Hespos; Michael J. Porco

(57) ABSTRACT

An object is to provide a medical liquid infusion apparatus suitable for a portable use and capable of suppressing an abrupt change in flow rate even when the environmental temperature rises. A medical liquid infusion apparatus 1 is provided with a driving portion 2 and configured to infuse a medical liquid inside a medical liquid container 3 to a patient by applying a pressure to the medical liquid container 3 using a driving force of the driving portion. The driving portion 2 includes a compressed gas cylinder 4 filled with a compressed gas, and it is configured in such a manner that the driving force is generated by the pressure inside the compressed gas cylinder 4.

6 Claims, 9 Drawing Sheets

FIG.4
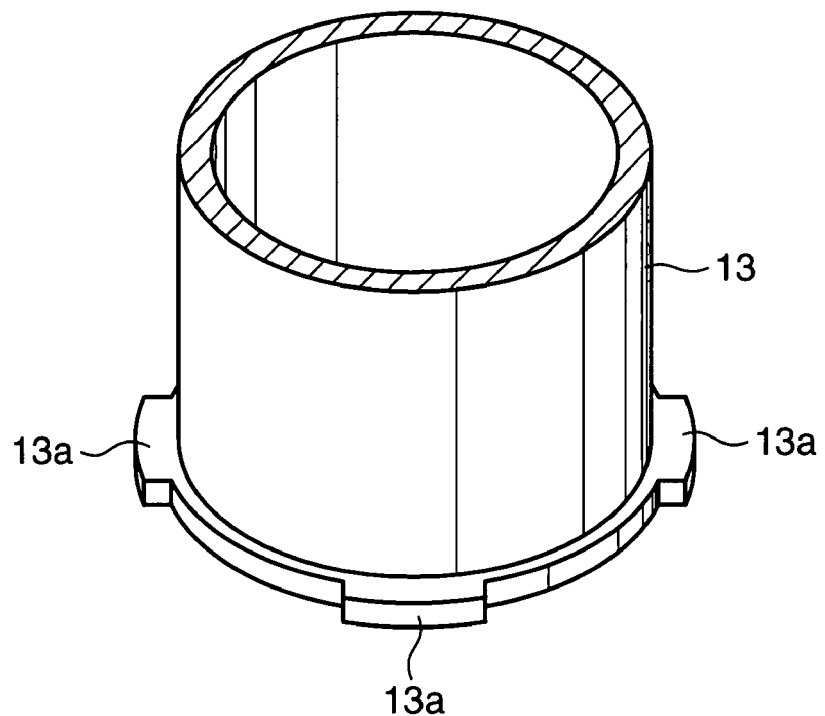
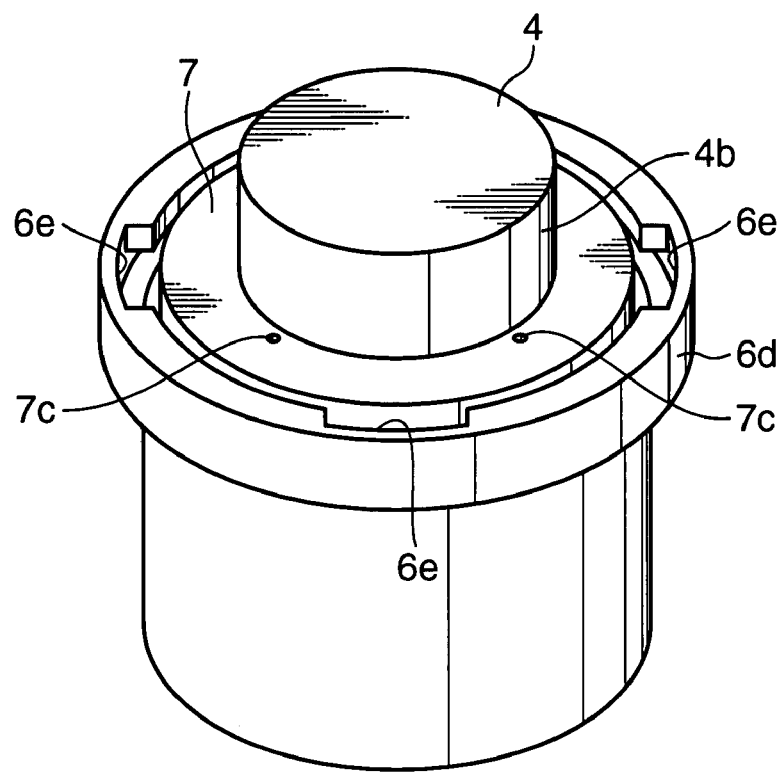

FIG.8

| | RISE IN ENVIRONMENTAL TEMPERATURE | | DROP IN ENVIRONMENTAL TEMPERATURE | |
|---|---|---|---|---|
| GAS INSIDE COMPRESSED GAS CYLINDER | PRESSURE INCREASES | ← | PRESSURE DECREASES | → |
| GAS INSIDE COMPRESSION CHAMBER | PRESSURE (DRIVING FORCE) DECREASES | → | PRESSURE (DRIVING FORCE) INCREASES | ← |
| MEDICAL LIQUID | VISCOSITY DECREASES | ← | VISCOSITY INCREASES | → |

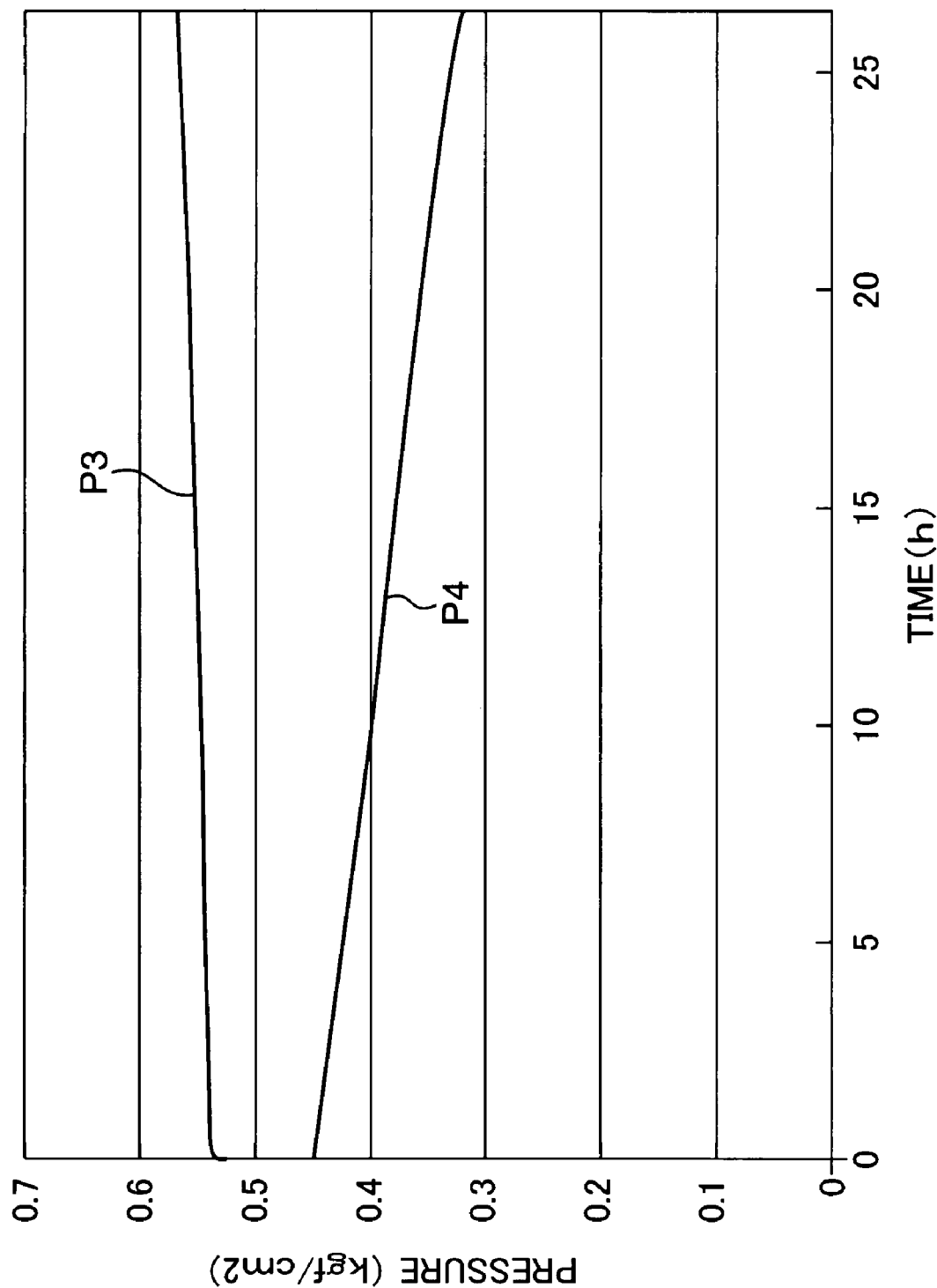

MEDICAL LIQUID INFUSION APPARATUS

BACKGROUND OF THE INVENTION

1. Field of the Invention

The present invention relates to a medical liquid infusion apparatus to infuse a medical liquid held in a medical liquid container into a patient.

2. Description of the Related Art

Generally, there has been known a medical liquid infusion apparatus provided with a driving source and configured to discharge a medical liquid inside a medical liquid container using a driving force of the driving source so as to infuse the medical liquid into a patient (for example, Patent Document 1 : JP-A-9-262288).

This medical liquid infusion apparatus uses a compressed gas cylinder filled with a liquefied carbon dioxide as the driving source. The medical liquid infusion apparatus is configured in such a manner that the interior of a compression chamber allowed to communicate with the compressed gas cylinder is brought into an under-pressure condition resulting from a saturated vapor pressure of the liquefied carbon dioxide so as to expand a bellows container that defines the compression chamber, and a pressure is applied to a medical liquid cartridge by the bellows container for the medical liquid to be discharged.

Because the medical liquid infusion apparatus uses a compact compressed gas cylinder that does not need power supply as the driving source, it is possible to achieve a configuration suitable for a portable use by the patient.

The medical liquid infusion apparatus of Patent Document 1 described above uses a pressure resulting from a saturated vapor pressure of the liquefied carbon dioxide as the driving source, and therefore has a characteristic that the driving force varies markedly when an environmental temperature rises above the environmental temperature at which the medical liquid is discharged at a predetermined flow rate (hereinafter, referred to as the reference operation temperature).

More specifically, because the saturated vapor pressure has a property that it increases in a quadratic curve with a rise in temperature (see L2 of FIG. 6), for example, a comparison between a change in vapor pressure when the environmental temperature dropped from 25° C. to 20° C. and a change in vapor pressure when the environmental temperature rose from 25° C. to 30° C. reveals that although a difference in temperature is the same (5° C.), a change in vapor pressure with a rise in temperature is far larger.

The medical liquid infusion apparatus of Patent Document 1 therefore has a markedly large change in flow rate when an environmental temperature rises above the reference operation temperature. Generally, an allowable range is set for the predetermined flow rate. However, in order to set an allowable range for the reference operation temperature in the medical liquid infusion apparatus of Patent Document 1 for the actual flow rate to fall within the allowable range, the allowable range has to be set smaller on the plus side and larger on the minus side.

The medical liquid infusion apparatus, however, is assumed that it is used in a case where it is mounted on the bedside of the patient or the like (that is, a case used under the room temperature condition) and in a case where it is used while being carried with the patient (that is, a case used under the thermal environment close to the body temperature of the patient). Meanwhile, the reference operation temperature is often set to room temperature at which the management by the medical staff or the like becomes easy. Accordingly, in the case of a portable use by the patient, an environmental temperature increases from the reference operation temperature.

In view of the foregoing, there is a request to set the allowable range of the reference operation temperature on the plus side to the fullest extent possible.

SUMMARY OF THE INVENTION

The invention was devised in view of the problems discussed above, and therefore has an object to provide a medical liquid infusion apparatus suitable for a portable use and capable of suppressing an abrupt change in flow rate even when an environmental temperature rises.

In order to solve the problems discussed above, a medical liquid infusion apparatus of the invention is provided with a driving portion and configured to infuse a medical liquid inside a medical liquid container into a patient by applying a pressure to the medical liquid container using a driving force of the driving portion, wherein the driving portion includes a compressed gas cylinder filled with a compressed gas alone, and the driving force is generated by a pressure inside the compressed gas cylinder.

According to the invention, because the pressure of the compressed gas is used as the driving force, it is possible to maintain a change of the driving force at an almost constant value in response to a difference in temperature regardless of whether the environmental temperature rises or drops.

More specifically, because the compressed gas inside the compressed gas cylinder shows a behavior almost in accordance with the equation of state of gas (PV=nRT), given that the volume V is constant, then the pressure P inside the compressed gas cylinder increases and decreases in proportion to a change in temperature T. Hence, according to the invention, because the driving force changes almost in proportion to a change in temperature, it is possible to suppress an abrupt change in flow rate even when the environmental temperature rises.

The phrase, "the compressed gas cylinder filled with the compressed gas alone", means that no liquefied gas is contained in the compressed gas cylinder.

Also, because a compressed gas cylinder that does not need power supply is used in the invention, it is possible to achieve a configuration suitable for a portable use by the patient.

BRIEF DESCRIPTION OF THE DRAWINGS

FIG. 4 is a perspective view showing the coupling structure of the driving portion and the medical liquid container.

FIG. 8 is an at-a-glance chart showing changes in pressure inside the compressed gas cylinder, pressure inside the compression chamber, and viscosity of the medical liquid when the environmental temperature has changed.

FIG. 9 is a graph showing the pressure of the medical liquid inside the cylinder during the medical liquid infusion, which is experiment data to compare a case where the piston is pushed into a cylinder having the inner surface of a non-tapered shape using a driving force of the driving portion 2 with a case where the piston 14 is pushed into the cylinder 14 having the inner surface of a tapered shape at a constant driving force.

DETAILED DESCRIPTION OF THE PREFERRED EMBODIMENTS

Hereinafter, a preferred embodiment of the invention will be described with reference to the drawings.

Figure 1:
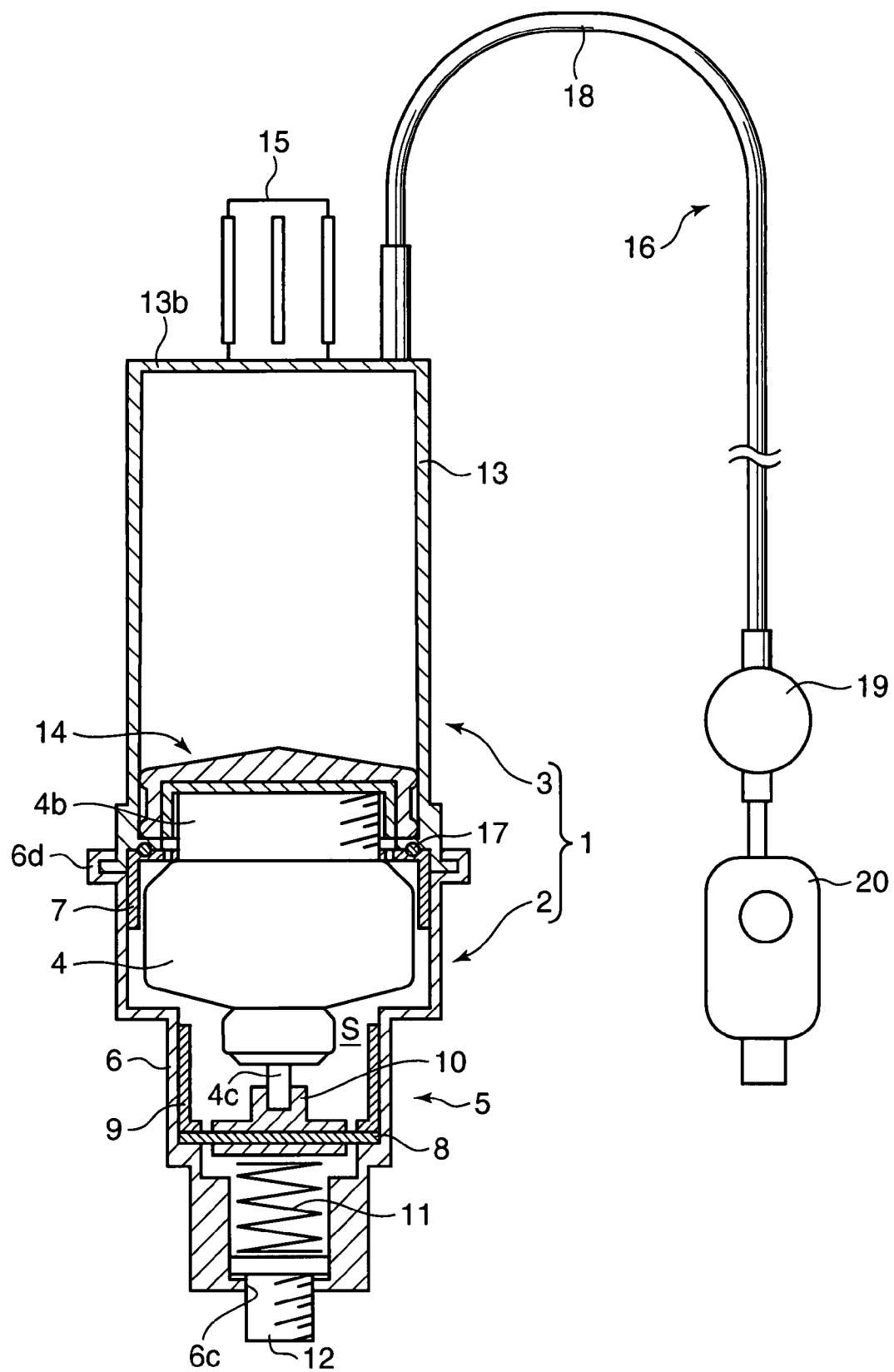
FIG. 1 is a sectional side view showing the overall configuration of a medical liquid infusion apparatus of the invention.
Figure 2:
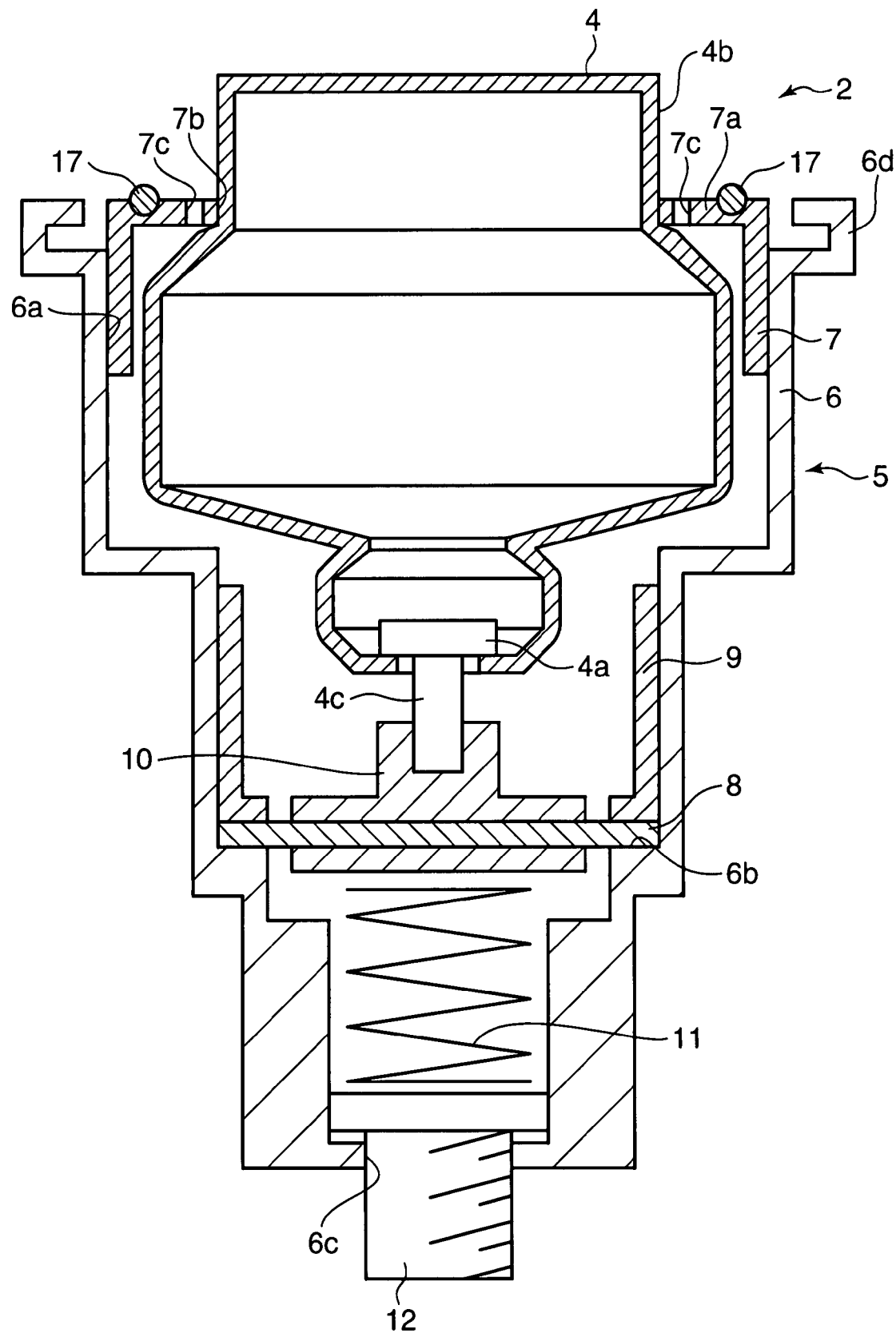
FIG. 2 is a sectional side view showing a driving portion of the medical liquid infusion apparatus of FIG. 1.
Figure 3:
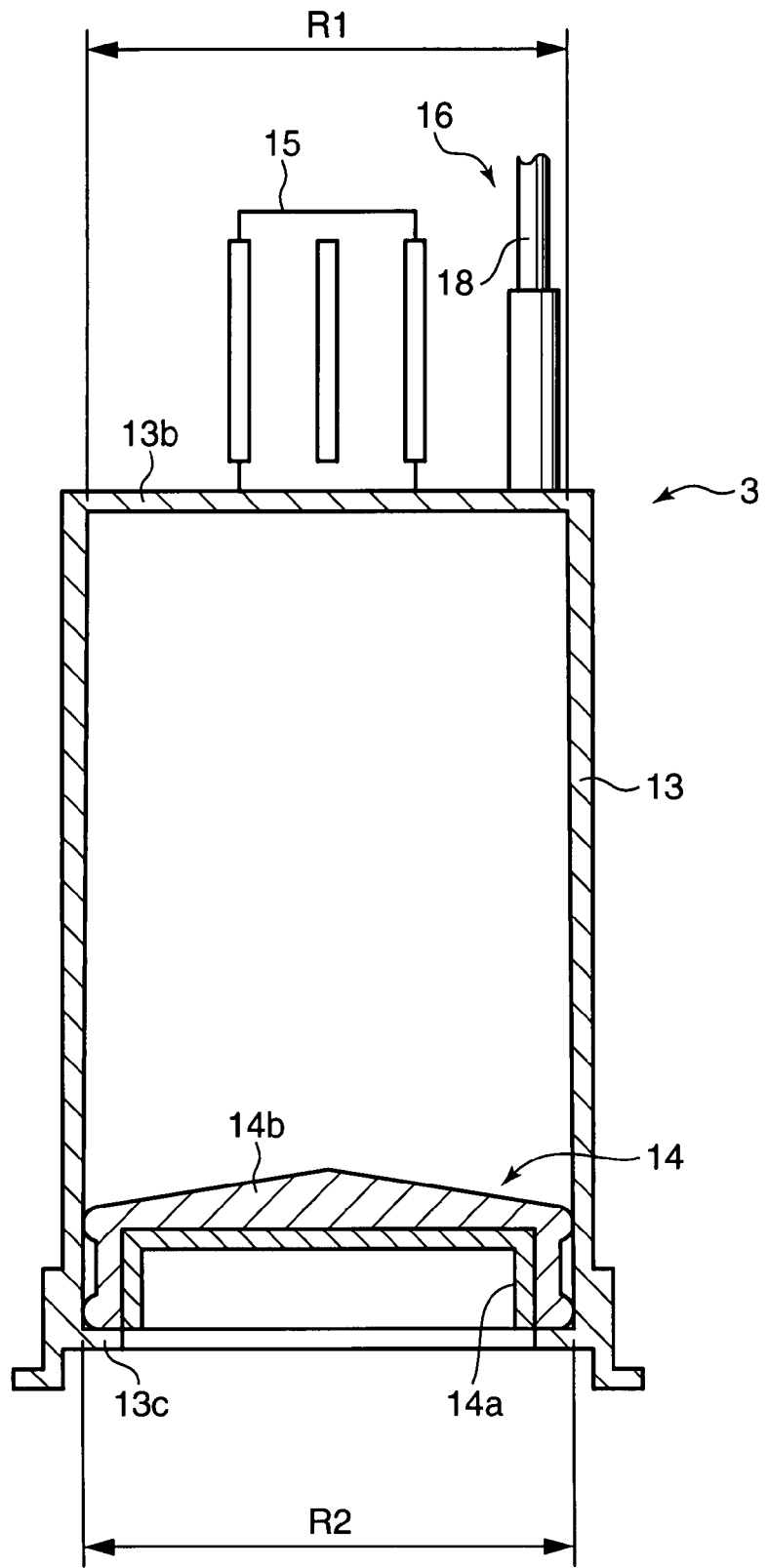
FIG. 3 is a sectional side view showing a medical liquid container of the medical liquid infusion apparatus of FIG. 1.

FIG. 1 is a sectional side view showing the overall configuration of a medical liquid infusion apparatus of the invention. FIG. 2 is a sectional side view showing a driving portion of the medical liquid infusion apparatus of FIG. 1. FIG. 3 is a sectional side view showing a medical liquid container of the medical liquid infusion apparatus of FIG. 1.

Referring to the respective drawings, because a medical liquid infusion apparatus 1 is configured to discharge a medical liquid by applying a pressure to a medical liquid container 3 using the pressure of a compressed gas filled in a compressed gas cylinder 4, it is possible to suppress an abrupt change in flow rate even when an environmental temperature rises. Hereinafter, a concrete configuration will be described.

The medical liquid infusion apparatus 1 is configured to combine a driving portion 2 and the medical liquid container 3 for use. More specifically, the medical liquid infusion apparatus 1 infuses a medical liquid inside the medical liquid container 3 into a patient by applying a pressure to the medical liquid container 3 using a driving force of the driving portion 2.

The driving portion 2 includes a compressed gas cylinder 4 filled with a compressed gas alone. The compressed gas cylinder 4 includes an on-off valve 4a that closes the compressed gas cylinder 4 using the pressure of the compressed gas when no external force is conferred thereto.

The driving portion 2 includes a main body portion 5 that houses the compressed gas cylinder 4 so that the on-off valve 4a is disposed in the interior thereof.

The main body portion 5 includes a cylindrical housing member 6 that widens to the tip in three steps and an attachment member 7 formed in the shape of a container with closed-end. The attachment member 7 is configured to fix the compressed gas cylinder 4 to the housing member 6 by being fit into a major opening portion 6a in the housing member 6 while a male screw portion 4b of the compressed gas cylinder 4 is threaded into a female screw portion 7b that penetrates through the bottom portion 7a at the center portion. Also, the attachment member 7 is provided with plural communication holes 7c (see FIG. 4) that penetrate through the bottom portion 7a.

An air-tight state is formed in a space between the compressed gas cylinder 4 and the attachment member 7 and in a space between the attachment member 7 and the housing member 6 using an unillustrated caulking material or the like.

The main body portion 5 includes a diaphragm valve 8 made of silicone rubber or the like having flexibility and a pressure pinching member 9 that fits the diaphragm valve 8 in the housing member 6. The pressure pinching member 9 is formed into an almost cylindrical shape, and is configured to form an air-tight state in a space between the diaphragm valve 8 and the housing member 6 by pinching the rim portion of the diaphragm valve 8 between the self and the shoulder portion 6b of the housing member 6 in the thickness direction while applying a pressure.

Further, the main body portion 5 includes a link member 10, a compression spring (pushing member) 11 that pushes the link member 10 toward the compressed gas cylinder 4, and a control knob 12 that adjusts a pushing force of the compression spring 11. The link member 10 pinches the diaphragm valve 8 in the thickness direction and is coupled to a plunger 4c of the on-off valve 4a. The control knob 12 is threaded into a female screw portion made in the inner surface of a minor opening portion 6c in the housing member 6, and it is therefore configured to adjust a pushing force of the compression spring 11 by changing a distance between the self and the link portion 10 by the adjustment of the degree of thread engagement.

A hook-shaped attachment piece 6d bulges from the outer circumferential surface at the end portion of the housing member 6 that widens toward the tip. As is shown in FIG. 4, plural notch portions 6e are made in the attachment piece 6d, and these notch portions 6e make it possible to receive stopper pieces 13a provided to a cylinder 13 described below. After the stopper pieces 13a are introduced through the corresponding notch portions 6e, the driving portion 2 and the medical liquid container 3 are rotated to displace the rotational positions of the stopper pieces 13a and the notch portions 6e. The driving portion 2 and the medical liquid container 3 are thus coupled to each other in an attachable and detachable manner.

The medical liquid container 3 includes a cylinder 13 having a bottom portion 13b, a piston 14 allowed to slide inside the cylinder 13, a filling port 15 made in the bottom portion 13b, and a medical liquid infusion line 16.

The cylinder 13 is formed in a tapered shape with its inner surface set at a gradient of about 0.2°, so that the inner dimension R1 on the bottom portion 13b side and the inner dimension R2 on the opening portion side establish R2>R1.

The opening portion of the cylinder 13 is provided with a positioning protrusion 13c that protrudes inward along the circumferential direction, and the positioning protrusion 13c prevents the piston 14 from falling off from the cylinder 13. It is configured in such a manner that when the driving portion 2 and the piston 14 are coupled to each other, the positioning protrusion 13c pinches an O-ring 17 between the self and the attachment member 7 while applying a pressure, thereby forming an air-tight state in a space between the self and the attachment member 7. The O-ring 17 is disposed on the outer position from the respective communication holes 7c in the attachment member 7.

The piston 14 is a structure of a coinjection molding formed by providing a packing 14b made of synthetic resin having relative flexibility on the outside of a supporting body 14a in the shape of a column with closed-end and made of synthetic resin having relative rigidity. The packing 14b forms a liquid-tight state in a space between the self and the inner surface of the cylinder 13 while being allowed to slide inside the cylinder 13 along the axial line thereof.

The filling port 15 includes a known check valve so that a medical liquid can be filled in a space between the bottom portion 13b and the piston 14 using a glass syringe or the like.

The medical liquid infusion line 16 is configured to guide the medical liquid filled in the cylinder 13 to a patient via a tube 18, during which the medical liquid is filtered by a filter 19 while the medical liquid is adjusted to a desired flow rate using a flow rate adjustment member 20. In this embodiment, the flow rate adjustment member 20 is configured to adjust the flow rate by producing a pressure loss by forcing the medical liquid to pass through a hole formed to have the minimal sectional area.

Hereinafter, the usage method and the driving principle of the medical liquid infusion apparatus 1 will be described.

Initially, a medical liquid is filled in the cylinder 13 through the filling port 15 while the piston 14 is fully pushed in toward the bottom portion 13b.

Subsequently, the driving portion 2 and the medical liquid container 3 are attached to each other, and in this instance, a compression chamber S capable of sealing a compressed gas flowing therein from the compressed gas cylinder 4 is defined in a space therebetween. More specifically, the compression chamber S is a space within the housing member 6 defined by the attachment member 7 and the diaphragm valve 8 and a space within the cylinder 13 linked to the firstly-mentioned space via the communication holes 7c and present before the piston 14.

The medical liquid infusion apparatus 1 is configured to discharge the medical liquid inside the cylinder 13 as the piston 14 is pushed in by a pressure inside the compression chamber S (that is, the driving force). Meanwhile, as the pressure inside the compression chamber S drops in association with the movement of the piston 14, a pressure is added from the compressed gas cylinder 4 so as to maintain a constant driving force.

Figure 5:
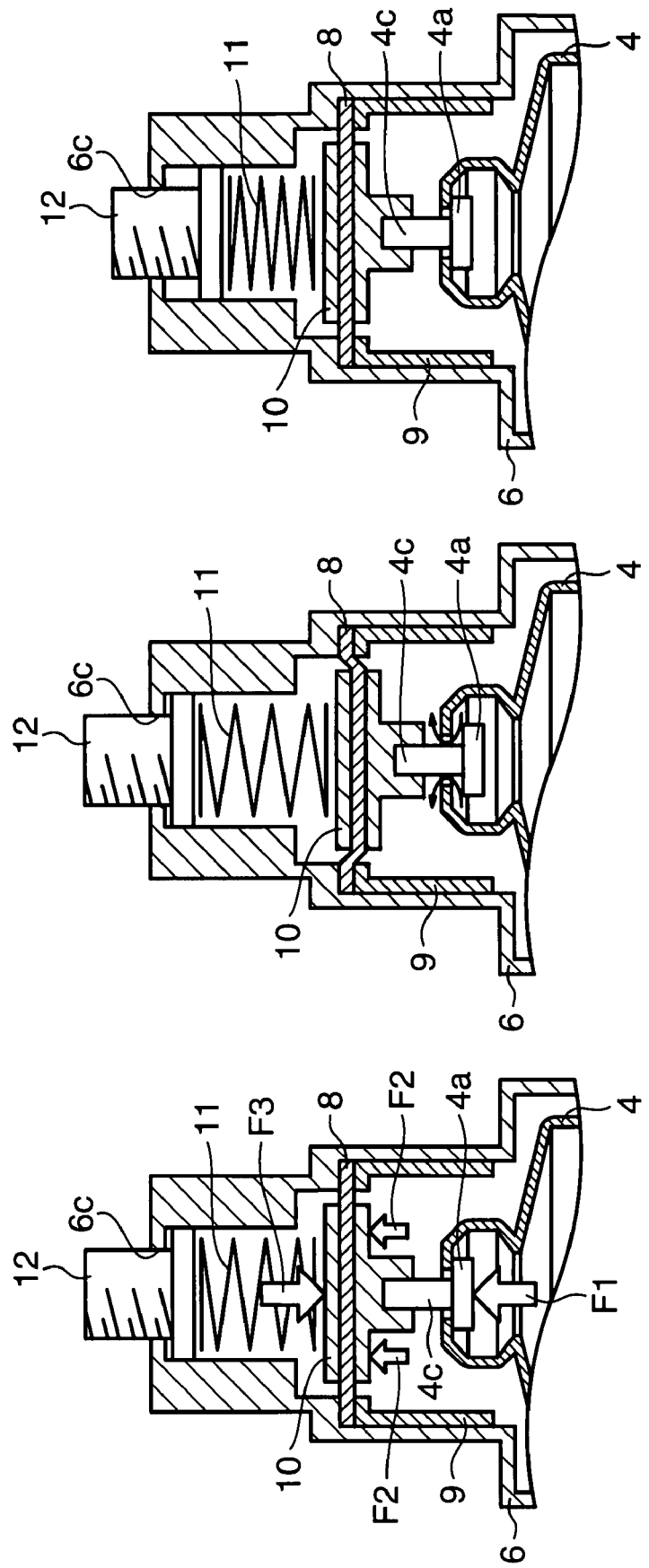
FIG. 5 is a sectional side view showing an operation of the driving portion, FIG. 5A showing a state where a first resultant force and a second resultant force balance out, FIG. 5B showing a state where an on-off valve is opened, and FIG. 5C showing a state where a pushing force of a compression spring is increased.

To be more concrete, as is shown in FIG. 5A, the driving portion 2 is configured in such a manner that the on-off valve 4a and the diaphragm valve 8 operate in synchronization with each other by the link member 10 for a resultant force (first resultant force) of a force F1 (a force resulting from the pressure of the compressed gas) to close the on-off valve 4a and a force F2 to expand the diaphragm valve 8 outward by the pressure inside the compression chamber S to balance out with a resultant force (second resultant force) F3 of a force to push the diaphragm valve 8 toward the compression chamber S using an atmospheric pressure and a pushing force of the compression spring 11 (F1+F2=F3).

Accordingly, when the pressure inside the compression chamber S drops as the compression chamber S expands in association with the movement of the piston 14, the balance of the forces comes undone (F1+F2<F3). Then, as is shown in FIG. 5B, the diaphragm valve 8 bends toward the compression chamber S and the on-off valve 4a opens.

The driving portion 2 therefore maintains an almost constant pressure inside the compression chamber S by appropriately opening and closing the on-off valve 4a of the compressed gas cylinder 4, and is thus able to maintain an almost constant driving force that pushes in the piston 14.

When the driving force of the driving portion 2 is changed, as is shown in FIG. 5C, the pushing force of the compression spring 11, that is, the resultant force F3 can be increased by screwing in the control knob 12. It is thus possible to increase the force F2 resulting from the pressure inside the pressurized chamber S and exerted to keep a balance with the resultant force F3.

Figure 6:
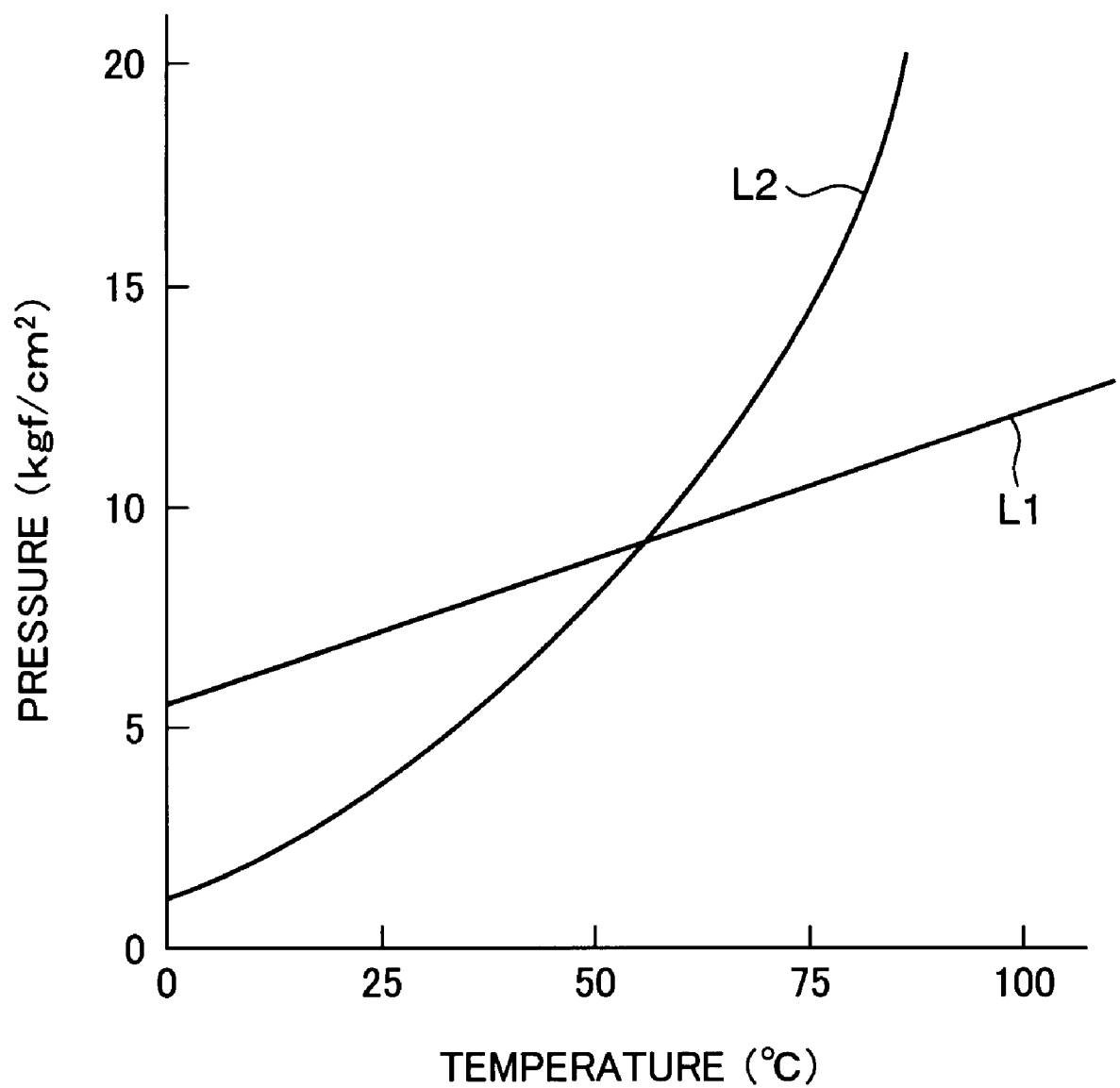
FIG. 6 is a graph showing a change in pressure inside a compressed gas cylinder when an environmental temperature has changed.

Incidentally, the compressed gas inside the compressed gas cylinder 4 behaves as is shown in FIG. 6 in response to a change in temperature under the use environment. FIG. 6 shows the pressure of the compressed gas cylinder 4 in a case where it is filled with nitrogen by way of example.

More specifically, in a case where nitrogen is adopted as the compressed gas, a pressure L1 inside the compressed gas cylinder 4 increases in proportion to a change in environmental temperature almost in accordance with the equation of state of gas (see Equation (1) below).

$$PV = nRT \quad (1)$$

where P: pressure
V: volume
(herein, volume of the compressed gas cylinder that remains constant)
n: number of moles
T: temperature Hence, by using the pressure of the compressed gas inside the compressed gas cylinder 4 as the driving force, it is possible to make a quantity of variance of the driving force almost constant in response to a difference in temperature regardless of whether the environmental temperature rises or drops. The description was given using nitrogen as an example of the compressed gas with reference to FIG. 6. It should be appreciated, however, that the invention is not limited to this configuration, and for example, a compressed air can be adopted as well.

A change in pressure of the compression chamber S and a change in discharge flow rate of the medical liquid infusion apparatus 1 will now be described with reference to FIG. 7 using a case where the environmental temperature actually rose from 20° C. to 40° C. by way of example.

Figure 7:
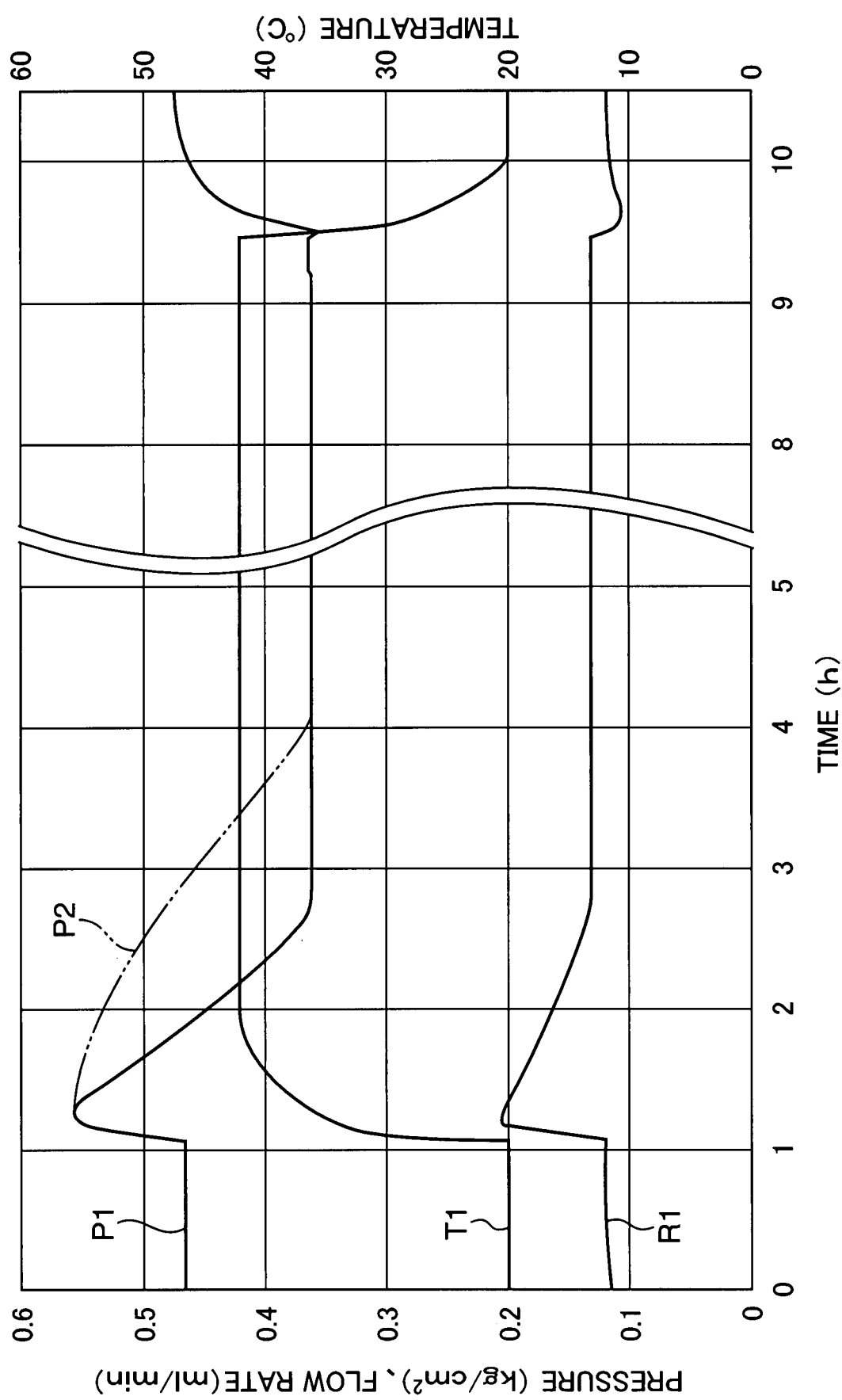
FIG. 7 is a graph showing a pressure inside a compression chamber and a flow rate of the medical liquid when the environmental temperature has changed.

Referring to FIG. 7, the medical liquid was infused over about one hour while the environmental temperature T1 was set at 20° C. initially. During the infusion, the pressure P1 inside the compression chamber and the flow rate R1 were maintained at about 0.47 kg/cm$^2$ and about 0.12 ml/min, respectively.

When the environmental temperature T1 was raised to 40° C., the pressure P1 first rose to about 0.56 kg/cm$^2$ in association with inflation of the gas inside the compression chamber S, and then started to drop gradually according to the stroke at which the piston 14 was pushed in. In association with this variance of pressure, the flow rate R1 also rose to about 0.21 ml/min first, and then started to drop gradually according to the stroke.

By pushing in the piston 14 with a specified stroke, the pressure P1 dropped to about 0.35 kg/cm$^2$, which is lower than the initial pressure (about 0.47 kg/cm$^2$), and this state was maintained thereafter. Herein, the pressure P1 becomes lower than the initial pressure to maintain the balance of the forces (F1+F2=F3) described above.

Meanwhile, in response to a change of the pressure P1, the flow rate R1 reached 0.13 ml/min when the specified stroke was completed, and this flow rate was maintained thereafter.

Herein, the pressure P1 was stabilized at a pressure lower than the initial pressure whereas the flow rate R1 increased from the initial flow rate (0.12 ml/min) with a rise of the environmental temperature T due to the influence of a change in viscosity of the medical liquid.

More specifically, as the environmental temperature T1 changed from 20° C. to 40° C., the viscosity of the medical liquid increased. To describe this phenomenon using distilled water as an example, the viscosity at 20° C. is 1.002 (cP) and the viscosity at 40° C. is 0.653 (cP). The medical liquid is forced to pass through the hole having the minimal cross section and made in the flow rate adjustment member 20, and in this instance, the fluid resistance decreases in response to a rise of the environmental temperature T1.

To be more concrete, according to the Hagen-Poiseuile law (see Equation (2) below), because a flow rate Q is in inverse proportion to the viscosity μ, theoretically speaking, the flow rate Q increases by 1.5 times (1.002÷0.653: increase of 50%)

when the viscosity changes. However, because the pressure P1 inside the compression chamber S decreases with an increase of the pressure inside the compressed gas cylinder 4 in the medical liquid infusion apparatus 1, the decrease in pressure and the increase in flow rate caused by a change in viscosity cancel each other out. An increase in flow rate therefore falls within an increase by about 1.08 times (0.13÷0.12: increase by 8%).

$$Q = p\pi R^4/(8\mu L) \quad (2)$$

Where Q: flow rate
p: pressure
R: radius of flow channel
μ: viscosity
L: length of flow channel Referring to FIG. 7, the environmental temperature T1 dropped to 20° C. again about nine and half hours later since the start of the medical liquid infusion. Accordingly, the pressure P1 and the flow rate R1 restored to nearly the same values after the infusion was started (P1: about 0.48 kg/cm², R1: about 0.12 ml/min). A time over which the environmental temperature T1 stayed at 40° C. was set to about eight hours on the assumption that the patient carries the medical liquid infusion apparatus 1 with him and goes to bed with it.

The influence on the medical liquid infusion apparatus 1 in response to the environmental temperature can be summarized as set forth in FIG. 8. That is to say, when the environmental temperature rises, the pressure inside the compressed gas cylinder 4 increases, according to which the pressure inside the compression chamber S decreases while the viscosity of the medical liquid decreases. As the decrease in pressure and the decrease in viscosity cancel each other out, a change in flow rate can be suppressed to the least extent possible.

Meanwhile, when the environmental temperature drops, the pressure inside the compressed gas cylinder 4 decreases, according to which the pressure inside the compression chamber S increases while the viscosity of the medical liquid increases. As the increase in pressure and the increase in viscosity cancel each other out, a change in flow rate can be suppressed to the least extent possible.

It should be noted that a pressure P2 of FIG. 7 indicates a variance of the pressure when the diaphragm valve 8 is made of nitrile rubber. The pressure P1 increases first with a rise of the environmental temperature T1 and then the pressure once increased restores to the predetermined pressure in about 1.5 hours, whereas a pressure P2 takes about three hours to restore to the predetermined pressure. This difference is attributed to the influence of the gas permeability of the diaphragm valve 8.

To be more concrete, butyl rubber, nitrile rubber, fluororubber, and silicone rubber generally used as a material having flexibility have gas permeability of 0.9 to 1.0, 0.3 to 3.5, 1, and 400 (unit: x10$^{-13}$ cc·cm/(cm²·sec·atm)), respectively, and silicone rubber has far higher gas permeability than the others. Hence, the medical liquid infusion apparatus 1 is able to discharge rapidly an extra pressure increased with a rise of the environmental temperature T1.

Further, because the driving portion 2 of the medical liquid infusion apparatus 1 uses the pressure of the compressed gas as the driving force, the pressure inside the compressed gas cylinder 4 drops as a quantity (number of moles) of the gas inside the compressed gas cylinder 4 decreases, in response to which the pressure inside the compression chamber S increases.

FIG. 9 shows the pressure of the medical liquid inside the cylinder during the medical liquid infusion, which is experiment data to compare a case where the piston is pushed into a cylinder having the inner surface of a non-tapered shape using a driving force of the driving portion 2 with a case where the piston 14 is pushed into the cylinder 13 having the inner surface of a tapered shape at a constant driving force.

More specifically, in a case where the piston is pushed into the cylinder having the flat inner surface using the driving portion 2, a pressure P3 of the medical liquid inside the cylinder increases gradually with an increase of a quantity of infused medical liquid. On the contrary, in a case where the piston 14 is pushed into the cylinder 13 at a constant pressure, sliding resistance between the piston 14 and the cylinder 13 increases as the former is pushed into the latter, and as a consequence, a pressure P4 of the discharged medical liquid gradually decreases.

Because the medical liquid infusion apparatus 1 is configured in such a manner that the piston 14 is pushed into the cylinder 13 having the inner surface formed in a tapered shape using the pressure inside the compression chamber S of the driving portion 2, changes in pressure corresponding to the pressure P3 and the pressure P4 cancel each other out. It is thus possible to suppress a change in flow rate of the infused medical liquid with an increase in quantity of the infused medical liquid (a decrease in quantity of the compressed gas) to the least extent possible.

In other words, in a case where the driving force is generated using a liquefied gas (carbon dioxide), there is an advantage that the driving force will not vary regardless of a remaining quantity of the liquefied gas (carbon dioxide) inside the compressed gas cylinder (the advantage achieved by the saturated vapor pressure) on the one hand, but on the other hand, in a case where the cylinder 13 is molded of synthetic resin, it is highly inevitable to design the inner surface of the cylinder 13 in a tapered shape due to the restriction (draft angle of the mold or the like) during the fabrication sequence, and a discharge pressure of the medical liquid decreases gradually when the driving force and the cylinder 13 are combined. In particular, because the cylinder 13 holding the medical liquid is requested to be thrown away after use for each patient in preventing infection, it is formed of a mold article of synthetic resin at a high frequency.

Hence, according to the medical liquid infusion apparatus 1 using the compressed gas alone as the driving force, it is possible to suppress a drop in discharge pressure attributed to the influence of the taper formed in the cylinder 13 to the least extent possible.

In this embodiment, it is configured in such a manner that the medical liquid is filled in the medical liquid container 3 through the filling port 15. It is, however, possible to fill the medical liquid container 3 with a specific medical liquid in advance. This configuration eliminates the need for a medical liquid filling work when the medical liquid infusion apparatus 1 is used. In addition, when this configuration is adopted, the filling port 15 may be omitted. However, there may arise a need to mix another medical liquid with the specific medical liquid in the act of medical treatment, and the filling portion 15 is not necessarily omitted.

As has been described, according to the medical liquid infusion apparatus 1, because the pressure of the compressed gas is used as the driving force, it is possible to maintain a change of the driving force almost at a constant value in response to a difference in temperature regardless of whether the environmental temperature rises or drops.

In other words, because the compressed gas inside the compressed gas cylinder 4 shows a behavior almost in accordance with the equation of state of gas, given that the volume of the compressed gas cylinder 4 is constant, then the pressure increases and decreases in proportion to a change in temperature.

Hence, according to the medical liquid infusion apparatus 1, because the driving force varies almost in proportion to a change in temperature, it is possible to suppress an abrupt change in flow rate even when the environment temperature rises.

In particular, when a liquefied gas is used, as is shown in FIG. 6, the pressure L2 inside the compressed gas cylinder changes along a saturated vapor pressure curve in a quadratic curve with a change in environmental temperature, and it therefore increases significantly when the environmental temperature rises. On the contrary, when the compressed gas is used as in the medical liquid infusion apparatus 1, because the pressure Li inside the compressed gas cylinder 4 increases and decreases almost in proportion to the environmental temperature, it is possible to suppress an abrupt change in flow rate even when the environmental temperature rises.

In addition, because the medical liquid infusion apparatus 1 uses the compressed gas cylinder 4 that does not need power supply, it is possible to achieve a configuration suitable for a portable use by the patient.

According to the configuration in which the driving portion 2 is attachable to and detachable from the medical liquid container 3, the driving portion 2 can be reused until the compressed gas is fully consumed by replacing the liquid medical container 3 with a new one after the medical liquid was infused. The disposable configuration can be therefore reduced, which can in turn reduce the cost of the medical liquid infusion apparatus 1.

According to the configuration in which a specific medical liquid has been previously filled in the medical liquid container 3, it is possible to omit a work to fill the medical liquid container 3 with the medical liquid when the medical liquid infusion apparatus is used, which can in turn reduce the burden of the medical staff.

According to the configuration in which the on-off valve 4a, the diaphragm valve 8, the compression spring 11, and the link member 10 are provided, and the pressure inside the pressurized chamber S is used as the driving force while the first resultant force (F1+F2) and the second resultant force F3 balance out, not only is it possible to make a change of the driving force with a change in environmental temperature almost constant in response to a change in temperature, but it is also possible to decrease the pressure inside the compressed gas cylinder 4 to a pressure at which a desired driving force can be produced.

More specifically, according to this configuration, because the first resultant force (F1+F2) and the second resultant force F3 balance out, a force resulting from the pressure inside the compression chamber S is the difference when a force resulting from an atmospheric pressure and a pushing force of the compression spring 11 are subtracted from a force resulting from the pressure inside the compressed gas cylinder 4 (F2=F3−F1). Hence, by appropriately choosing a pushing force of the compression spring 11, it is possible to set the driving force to desired magnitude.

According to the configuration in which the flow rate adjustment member 20 is provided, it is possible to further enhance the accuracy of the flow rate when the environmental temperature has changed.

More specifically, as the pressure of the compressed gas increases with a rise in environmental temperature, the first resultant force is to increase. However, because the first resultant force has to maintain a balance with the second resultant force F3 while the second resultant force F3 remains constant, a force trying to expand the diaphragm valve 8 outward, that is, the pressure inside the compression chamber S drops as a consequence.

Meanwhile, the viscosity of the medical liquid decreases with a rise in environmental temperature, and the fluid resistance of the medical liquid with respect to the flow rate adjustment member 20 becomes smaller, which increases the flow rate of the medical liquid.

Hence, according to the configuration as above, the driving force shifts (decreases) in a direction for the flow rate of the medical liquid to decrease and the viscosity of the medical liquid shifts (decreases) in a direction for the flow rate of the medical liquid to increase with a rise in environmental temperature. As these changes cancel each other out, a change in flow rate of the medical liquid with a rise in environmental temperature can be suppressed to the least extent possible.

According to the configuration in which the cylinder 13 and the piston 14 are provided, because the interior of the cylinder 13 is formed in a tapered-shape, it is possible to suppress a decrease in flow rate of the medical liquid with a decrease of a remaining quantity of the medical liquid.

More specifically, the pressure of the compressed gas inside the compressed gas cylinder 4 drops in association with the stroke by which the piston 14 is pushed in (an increase of a quantity of used compressed gas). However, as has been described, the pressure inside the compression chamber S increases with a drop in pressure inside the compressed gas cylinder 4. Meanwhile, the sliding resistance of the piston 14 with respect to the cylinder 13 increases in response to the stroke because of the taper formed inside the cylinder 13.

Hence, according to this configuration, the driving force shifts (increases) in a direction for the flow rate of the medical liquid to increase while the sliding resistance of the piston 14 shifts (increases) in a direction for the flow rate of the medical liquid to reduce with a decrease of the remaining quantity of the medical liquid. As these changes cancel each other out, a decrease in flow rate of the medical liquid can be suppressed.

According to the configuration in which the diaphragm valve 8 is made of a material having high gas permeability at least in part, even when the pressure inside the compression chamber S has increased, it is possible to maintain the flow rate of the medical liquid as accurate as possible.

More specifically, when the environmental temperature rises, the pressure inside the compression chamber S increases, and according to the configuration described above, an extra pressure can be released actively through the diaphragm valve 8. It is thus possible to allow the compression chamber S to restore to its specified pressure quickly.

Hence, according to the configuration as above, even when the environmental temperature rises, it is possible to suppress an increase in flow rate temporarily, which in turn makes it possible to maintain the flow rate as accurate as possible.

An on-off valve can be provided to the communication holes 7c of the medical liquid infusion apparatus 1. When configured in this manner, it is possible to prevent the compressed gas from releasing wastefully when the driving portion 2 and the medical liquid container 3 are attached to each other.

Alternatively, the communication holes 7c may be omitted, and the compressed gas may be flown through a space between the female screw portion 7b in the housing member 6 and the male screw portion 4b of the compressed gas cylinder 4.

To be more specific, the invention according to one embodiment is a medical liquid infusion apparatus provided with a driving portion and configured to infuse a medical liquid inside a medical liquid container into a patient by applying a pressure to the medical liquid container using a driving force of the driving portion, wherein the driving portion includes a compressed gas cylinder filled with a compressed gas alone, and the driving force is generated by a pressure inside the compressed gas cylinder.

According to the invention, because the pressure of the compressed gas is used as the driving force, it is possible to maintain a change of the driving force at an almost constant value in response to a difference in temperature regardless of whether the environmental temperature rises or drops.

More specifically, because the compressed gas inside the compressed gas cylinder shows a behavior almost in accordance with the equation of state of gas (PV=nRT), given that the volume V is constant, then the pressure P inside the compressed gas cylinder increases and decreases in proportion to a change in temperature T.

Hence, according to the invention, because the driving force changes almost in proportion to a change in temperature, it is possible to suppress an abrupt change in flow rate even when the environmental temperature rises.

Also, because a compressed gas cylinder that does not need power supply is used in the invention, it is possible to achieve a configuration suitable for a portable use by the patient.

In the medical liquid infusion apparatus described above, it is preferable that the driving portion is configured so as to be attachable to and detachable from the medical liquid container.

According to the configuration in which the driving portion is made attachable to and detachable from the medical liquid container, by replacing the medical liquid container with a new one after the medical liquid was infused, the driving portion can be reused until the compressed gas is fully consumed. It is thus possible to reduce a disposable configuration, which can in turn reduce the cost of the medical liquid infusion apparatus.

In the medical liquid infusion apparatus described above, it is preferable that the medical liquid container has been previously filled with a specific medical liquid.

According to the configuration in which the medical liquid container has been previously filled with the specific medical liquid, it is possible to omit a work to fill the medical liquid container with a medical liquid when the medical liquid infusion apparatus is used, which can in turn reduce the burden of the medical staff.

In the medical liquid infusion apparatus described above, it is preferable that: the compressed gas cylinder includes an on-off valve configured to close the compressed gas cylinder using a pressure of the compressed gas when no external force is conferred thereto; the driving portion includes a main body portion allowed to communicate with an interior of the compressed gas cylinder by opening the on-off valve, a diaphragm valve that defines a compression chamber capable of sealing the compressed gas flown from the compressed gas cylinder in a space between the main body portion and the medical liquid container, a pushing member that pushes the diaphragm valve toward the compression chamber from an outside open to atmosphere, and a link member that allows the on-off valve and the diaphragm valve to operate in synchronization with each other in such a manner that a first resultant force obtained by adding a force to close the on-off valve and a force to expand the diaphragm valve outward using the pressure inside the compression chamber is balanced out with a second resultant force to push the diaphragm valve toward the compression chamber using an atmospheric pressure and a pushing force of the pushing member; and the pressure inside the compression chamber is used as the driving force.

According to the configuration in which the on-off valve, the diaphragm valve, the pushing member, and the link member are provided and the pressure inside the compression chamber is used as the driving force while the first resultant force and the second resultant force balance out, not only is it possible to make a change of the driving force with a change in environmental temperature almost constant in response to a difference in temperature, but it is also possible to decrease the pressure inside the compressed gas cylinder to a pressure at which a desired driving force can be produced.

More specifically, according to the configuration as above, because the first resultant force and the second resultant force balance out, a force resulting from the pressure inside the compression chamber is the difference when a force resulting from the pressure inside the compressed gas cylinder is subtracted from a force resulting from an atmospheric pressure and a pushing force of the pushing member. Hence, by appropriately choosing the pushing force of the pushing member, it is possible to set the driving force at desired magnitude.

In the medical liquid infusion apparatus described above, it is preferable that the medical liquid container has a hole formed to have a minimal sectional area, and a flow rate adjustment member capable of adjusting a flow rate of the medical liquid by forcing the medical liquid discharged according to the driving force to pass through the hole so as to produce a pressure loss.

According to the configuration in which the flow rate adjustment member is provided, it is possible to further enhance the accuracy of flow rate when the environmental temperature has changed.

More specifically, as has been described, the pressure of the compressed gas shows a behavior that it increases with a rise in temperature. When the pressure increases, the first resultant force is to increase. However, the first resultant force has to maintain a balance with the second resultant force, and the second resultant force (pushing force+atmospheric pressure) remains constant. As a result, a force to expand the diaphragm valve outward, that is, the pressure inside the compression chamber drops.

Meanwhile, the viscosity of the medical liquid decreases with a rise in environmental temperature, which lessens the fluid resistance of the medical liquid with respect to the flow rate adjustment member. A flow rate of the medical liquid consequently increases.

Hence, according the configuration as above, the driving force shifts (decreases) in a direction for the flow rate of the medical liquid to decrease while the viscosity of the medical liquid shifts (decreases) in a direction for the flow rate of the medical liquid to increase with a rise in environmental temperature. As these changes cancel each other out, a change in flow rate of the medical liquid with a rise in environmental temperature can be suppressed to the least extent possible. Also, even when the environmental temperature drops, because the driving force increases while the viscosity of the medical liquid increases, a change in flow rate of the medical liquid can be suppressed in the same manner.

In the medical liquid infusion apparatus described above, it is preferable that the medical liquid container includes a cylinder to hold the medical liquid and a piston that slides within the cylinder along an axial direction thereof to allow the medical liquid to be discharged from a tip end side of the cylinder, and an interior of the cylinder is formed in a tapered-shape that narrows toward the tip end side.

According to the configuration in which the cylinder and the piston are provided, because the interior of the cylinder is formed in a tapered-shape, it is possible to suppress a decrease in flow rate of the medical liquid with a decrease of the remaining amount of the medical liquid.

More specifically, the pressure of the compressed gas inside the compressed gas cylinder drops with a stroke with which the piston is pushed in (an increase in quantity of used compressed gas). As has been described, however, when the pressure inside the compressed gas cylinder decreases, the pressure inside the compression chamber increases. Meanwhile, the sliding resistance of the piston with respect to the cylinder increases with the stroke due to the taper formed inside the cylinder.

Hence, according to this configuration, because the driving force shifts (increases) in a direction for a flow rate of the medical liquid to increase while the sliding resistance of the piston shifts (increases) in a direction for the flow rate of the medical liquid to decrease with a decrease of the remaining quantity of the medical liquid. As these changes cancel each other out, a decrease in flow rate of the medical liquid can be suppressed.

In the medical liquid infusion apparatus described above, it is preferable that the diaphragm valve is made of a material having high gas permeability at least in part.

According to the configuration in which the diaphragm valve is made of a material having high gas permeability at least in part, even when the pressure inside the compression chamber has increased, it is possible to maintain the flow rate of the medical liquid as accurate as possible.

To be more specific, when the environmental temperature rises, as has been described, not only the pressure inside the compressed gas cylinder, but also the pressure inside the compression chamber increases for a specific time in accordance with the equation of state of gas. The term, "specific time", referred to herein means a time needed for a risen pressure to restore to a normal pressure (a pressure while the first and second resultant forces balance out) in response to an application of pressure to the medical liquid container. According to the configuration as above, because the extra pressure can be actively released through the diaphragm valve, the compression chamber can restore to the normal pressure quickly.

Hence, according to the configuration as above, even when the environmental temperature rises, it is possible to suppress an increase in flow rate temporarily, which in turn makes it possible to maintain the flow rate as accurate as possible.

The phrase, "a material having high gas permeability", means a material having an air-tightness high enough to maintain a balance at least between the first and second resultant forces.

The invention claimed is:

1. A medical liquid infusion apparatus provided with a driving portion and configured to infuse a medical liquid inside a medical liquid container into a patient by applying a pressure to the medical liquid container using a driving force of the driving portion, wherein:

the driving portion includes a compressed gas cylinder filled with a compressed gas alone, and the driving force is generated by a pressure inside the compressed gas cylinder, the compressed gas cylinder including an on-off valve configured to close the compressed gas cylinder using a pressure of the compressed gas, when no external force is conferred thereto, wherein the driving portion further includes:

a main body portion allowed to communicate with an interior of the compressed gas cylinder by opening the on-off valve;

a diaphragm valve that defines a compression chamber capable of sealing the compressed gas flown from the compressed gas cylinder in a space between the main body portion and the medical liquid container;

a pushing member that pushes the diaphragm valve toward the compression chamber from an outside open to atmosphere; and a link member that allows the on-off valve and the diaphragm valve to operate in synchronization with each other in such a manner that a first resultant force obtained by adding a force to close the on-off valve and a force to expand the diaphragm valve outward using the pressure inside the compression chamber is balanced out with a second resultant force to push the diaphragm valve toward the compression chamber using an atmospheric pressure and a pushing force of the pushing member, and wherein the pressure inside the compression chamber is used as the driving force.

2. The medical liquid infusion apparatus according to claim 1, wherein:

the driving portion is configured so as to be attachable to and detachable from the medical liquid container.

3. The medical liquid infusion apparatus according to claim 1, wherein:

the medical liquid container has been previously filled with a specific medical liquid.

4. The medical liquid infusion apparatus according claim 1, wherein:

the medical liquid container has a hole formed to have a minimal sectional area, and a flow rate adjustment member capable of adjusting a flow rate of the medical liquid by forcing the medical liquid discharged according to the driving force to pass through the hole so as to produce a pressure loss.

5. The medical liquid infusion apparatus according claim 1, wherein:

the medical liquid container includes a cylinder to hold the medical liquid and a piston that slides within the cylinder along an axial direction thereof to allow the medical liquid to be discharged from a tip end side of the cylinder; and an interior of the cylinder is formed in a tapered-shape that narrows toward the tip end side.

6. The medical liquid infusion apparatus according claim 1, wherein:

the diaphragm valve is made of a material having high gas permeability at least in part.

* * * * *